(12) United States Patent
Lederman

(10) Patent No.: US 8,481,599 B2
(45) Date of Patent: Jul. 9, 2013

(54) COMPOSITIONS AND METHODS FOR INCREASING COMPLIANCE WITH THERAPIES USING ALDEHYDE DEHYDROGENASE INHIBITORS AND TREATING ALCOHOLISM

(75) Inventor: Seth Lederman, New York, NY (US)

(73) Assignee: Tonix Pharmaceuticals Inc., New York, NY (US)

( * ) Notice: Subject to any disclaimer, the term of this patent is extended or adjusted under 35 U.S.C. 154(b) by 0 days.

(21) Appl. No.: 13/340,999

(22) Filed: Dec. 30, 2011

(65) Prior Publication Data

US 2012/0101154 A1 Apr. 26, 2012

Related U.S. Application Data

(62) Division of application No. 12/145,792, filed on Jun. 25, 2008, now Pat. No. 8,093,300, which is a division of application No. 10/287,153, filed on Nov. 4, 2002, now abandoned.

(60) Provisional application No. 60/338,901, filed on Nov. 5, 2001.

(51) Int. Cl.
*A61K 31/135* (2006.01)
*A61K 31/16* (2006.01)

(52) U.S. Cl.
USPC ............ 514/654; 514/649; 514/599; 514/811

(58) Field of Classification Search
USPC .................................. 514/649, 654, 599, 811
See application file for complete search history.

(56) References Cited

U.S. PATENT DOCUMENTS

| | | | |
|---|---|---|---|
| 2,567,814 A | | 9/1951 | Jacobsen et al. |
| 3,155,584 A | | 11/1964 | Martin |
| 4,076,840 A | | 2/1978 | Carlsson et al. |
| 4,565,689 A | | 1/1986 | Revici |
| 4,678,809 A | * | 7/1987 | Phillips .................. 514/599 |
| 4,861,800 A | | 8/1989 | Buyske |
| 4,868,218 A | | 9/1989 | Buyske |
| 5,128,145 A | | 7/1992 | Edgren et al. |
| 5,190,763 A | | 3/1993 | Edgren et al. |
| 5,192,550 A | | 3/1993 | Edgren et al. |
| 5,204,369 A | | 4/1993 | Vallee et al. |
| 5,242,950 A | | 9/1993 | Hastings |
| 5,886,028 A | | 3/1999 | Vallee et al. |
| 5,952,388 A | | 9/1999 | Loscher |
| 6,121,010 A | | 9/2000 | Vallee et al. |
| 6,239,181 B1 | | 5/2001 | Bobotas |
| 6,255,497 B1 | | 7/2001 | Vallee et al. |
| 6,500,868 B2 | * | 12/2002 | Bobotas .................. 514/654 |
| 8,093,300 B2 | | 1/2012 | Lederman |
| 2003/0087814 A1 | | 5/2003 | Lederman |
| 2009/0005441 A1 | | 1/2009 | Lederman |

FOREIGN PATENT DOCUMENTS

| | | |
|---|---|---|
| EP | A 404807 | 10/1989 |
| EP | A 509761 | 4/1992 |
| EP | 0520325 A1 | 6/1992 |
| EP | A 593807 | 10/1992 |
| WO | WO 92/05787 | 4/1992 |
| WO | WO 92/21333 | * 12/1992 |
| WO | WO 96/35425 | 11/1996 |
| WO | WO 96/37199 | 11/1996 |
| WO | WO 99/21540 | 5/1999 |
| WO | WO 00/45846 | 8/2000 |
| WO | WO 00/71109 | 11/2000 |
| WO | WO 03/039525 | 5/2003 |

OTHER PUBLICATIONS

U.S. Appl. No. 60/338,901, Lederman.
NIAAA "Etiology and Natural history of alcoholism," http://pubs.niaaa.nih.gov/publications/social/Module2Etiology&NaturalHistory/Module2.html, 2002.
Demaster, et al., Biochem. Biophys. Res. Com. 107:1333-1339 (1982).
Ferguson, Canad. M.A.J. 74:793-795 (1956).
Hart, et al., Alcohol 7:165 (1990).
Jimerson, D.C., et al., Biomed. Mass.Spectrom. 8:256-259 (1981).
Keung, Chemico-Bio. Int. 130-132:919-930 (2001).
Keung, W.M., et al., Proc. Natl. Acad. Sci. USA 95:2198-2203 (1998).
Kick, S., Hospital Practice 95-106(1999).
Madan, et al., Drug Metab. Dispos. 23:1153-1162 (1995).
Major, L.F., et al., J. Neurochem. 32:229-231 (1979).
McRae et al., "Alcohol and Substance Abuse," in: Advances in the Pathophysiology and Treatment of Psychiatric Disorders: Implications for Internal Medicine,85(3):779-801(2001).
Murphy, D.L., et al., Biochem. Med. 16:254-265 (1976).
Murphy, D.L., et al., Clinical Pharmacology in Psychiatry, 3rd Series, Eds. Dahl, Gram, Paul, and Potter, Springer-Verlag: 1987.
Murphy, D.L., et al., Psychopharm. 62:129-132 (1979).
Reilly, Lancet 911-912 (1976).
Sinclair, et al., Adv. Exp. Med. Biol. 132:481-487 (1980).
Yourick, et al., Alcohol 4:463 (1987).
Yourick, et al., Biochem. Pharmacol. 38:413 (1989).
International Search Report, International Application No. PCT/US02/35376 of Jun. 23, 2004.
Swift, R. M. (May 6, 1999). Drug Therapy for Alcohol Dependence. The New England Journal of Medicine 340[18], 1482-1490.
Krystal, J. H., et al. (2001). Naltrexone in the Treatment of Alcohol Dependence. The New England Journal of Medicine, 345, 1734-1739.
Hermos, J. A., et al. (2004). Patterns of dispensed disulfiram and naltrexone for alcoholism treatment in a veteran patient population. Alcohol Clin.Exp.Res., 28, 1229-1235.
Garbutt, J. C., West, S. L., Carey, T. S., Lohr, K. N., & Crews, F. T. (1999). Pharmacological treatment of alcohol dependence: a review of the evidence. JAMA, 281, 1318-1325.

(Continued)

*Primary Examiner* — Shengjun Wang
(74) *Attorney, Agent, or Firm* — Kelley Drye & Warren LLP

(57) ABSTRACT

Compositions and methods for treating, preventing, or reducing alcoholism, in particular methods for increasing patient compliance with therapies that require the intake of an ALDH inhibitor comprising the step of administering a monoamine oxidase B inhibitor.

11 Claims, No Drawings

OTHER PUBLICATIONS

Berglund, M., et al. (2003). Pharmacological treatment of alcohol dependence. Alcohol Clin.Exp.Res. 27[10], 1645-1656.

DeLuca, A. (1996). Medications that can Help Us Avoid . . . Addiction, Pain, & Public Health website. http://www.doctordeluca.com/Documents/SobrietyMeds_11-1.htm.

Schultz, W. (1998). Predictive reward signal of dopamine neurons. J Neurophysiol, 80,1-27.

Bowirrat, A. & Oscar-Berman, M. (2004). Relationship between dopaminergic neurotransmission, alcoholism, and reward deficiency syndrome. Am J Med Genet.

Cohen, C., et al. (1999). Reduction of oral ethanol self-administration in rats by monoamine oxidase inhibitors. Pharmacol.Biochem. Behav., 64, 535-539.

Porsolt, R. D., et al. (1984). Discrimination of the amphetamine cue. Effects of A, B and mixed type inhibitors of monoamine oxidase. Neuropharmacology, 23, 569-573.

Oldfield, V., et al., "Oxycodone/Ibuprofen combination tablet: . . . ," Drugs 2005; 65(16): 2337-2354.

Litkowski, L.J., et al., "Analgesic Efficacy and Tolerability of Oxycodone 5 mg/ . . . ," Clin. Ther., Apr. 2005; 27(4): 418-429.

Kapil, R., et al.,"Pharmacokinetic Properties of Combination Oxycodone plus Racemic Ibuprofen . . . ," Clin. Ther., Dec. 2004; 26(12): 2015-2025.

Van, D.T., et al., "Combination Oxycodone 5 mg/Ibuprofen 400 mg . . . ," Clin. Ther., Dec. 2004, 26(12): 2003-2014.

Zelcer, S., et al., "Selective Potentiation of Opioid Analgesia . . . " Brain Res., Apr. 8, 2005; 1040(1-2): 151-156.

Sachs, C.J., "Oral Analgesics for Acute Nonspecific Pain," Am. Fam. Physician, Mar. 1, 2005; 71(5): 913-918.

Singla, N., et al., "Combination Oxycodone 5 mg/Ibuprofen 400 mg . . . ," Clin. Ther., Jan. 2005; 27(1): 45-57.

Huynh, M.P., et al., "Current Concepts in Acute Pain Management," J. Calif Dent Assoc. May 2003; 31(5): 419-427.

Palangio, M., et al., "Combination Hydrocodone and Ibuprofen . . . ," Clin. Ther. Jan. 2002; 24(1): 87-99.

Barkin, R.L., "Acetaminophen, Aspirin, or Ibuprofen . . . ," Am. J. Ther., Nov. 2001; 8(6): 433-442.

Palangio, M., et al., "Combination Hydrocodone and Ibuprofen . . . ," Clin. Ther. May 2000; 22(5): 600-612.

Tobias, J.D., "Weak Analgesics and Nonsteroidal . . . ," Pediatr Clin. North Am. Jun. 2000; 47(3): 527-543.

Dionne, R.A., "Additive Analgesic Effects of Oxycodone . . . ," J. Oral Maxillofac Surg., Jun. 1999; 57(6): 673-678.

Stambaugh, J.E., et al., "The Combination of Ibuprofen and Oxycodone/Acetaminophen In the Management of Chronic Cancer Pain," Clin. Pharmacol. Ther., Dec. 1998; 44(6):665-659.

Snell, et al., "Relationships Between Effects of Smoking, Gender, and Alcohol . . . ," Alcoholism: Clinical & Experimental Research, 26(7): 1105-1113, Jul. 2002.

Ucar, et al., "Serotenergic Functions in Alcoholism Subtypes," FEBS Journal, 272, Abstract #M3-026P, 2005.

Anton, Raymond F., "What Is Craving? Models and Implications for Treatment . . . ," Alcohol Research & Health, Fall, 1999, pp. 1-12.

Azrin N. H. (1976). Improvements in the community-reinforcement approach to alcoholism. Behay.Res.Ther., 14, 339-348.

Azrin, N.H., et al. (1982) "Alcoholism Treatment by Disulfiram and Community Reinforcement Therapy," J. Behav. Ther. Exp. Psychiatry, vol. 13, pp. 105-112.

Brewer, C. (1993). Recent developments in disulfiram treatment. Alcohol & Alcoholism, 28, 383-395.

Chick, J. (1998). Treatment of alcoholic violent offenders: ethics and efficacy. Alcohol & Alcoholism, 33, 20-25.

Fowler, C. J., et al. (1983). The metabolism of dopamine by both forms of monoamine oxidase in the rat brain and its inhibition by cimoxatone. J Neurochem., 40, 1534-1541.

Quitkin, F. M., et al. (1984). l-Deprenyl in atypical depressives. Arch of General Psychiatry, 41, 777-781.

Sunderland, T., et al. (1994). High-dose selegiline in treatment-resistant older depressive patients. Arch.Gen.Psychiatry, 51, 607-615.

Yasar, S. & Bergman, J. (1994). Amphetamine-like effect of 1-deprenyl (selegiline) in drug discrimination studies. Clin. Pharmacol.Ther., 56, 768-773.

Wu, W. R. & Zhu, X. Z. (1999). The amphetamine-like reinforcing effect and mechanism of L-deprenyl on conditioned place preference in mice. Eur.J Pharmacol., 364, 1-6.

Yasar, S., et al. (1994). Evaluation of deprenyl for cocaine-like discriminative stimulus effects in rats. Eur.J Pharmacol., 259, 243-250.

Fuller, R. K., et al. (1986). Disulfiram treatment of alcoholism. JAMA: The Journal of the American Medical Association, 256, 1449-1455.

Fuller, R. K. & Gordis, E. (2004). Does disulfiram have a role in alcoholism treatment today? Addiction, 99, 21-24.

Hughes, J. C. & Cook, C. C. (1997). The efficacy of disulfiram: a review of outcome studies. Addiction, 92, 381-395.

Glover, V., Elsworth, J. D., & Sandler, M. (1980). Dopamine oxidation and its inhibition by (−)-deprenyl in man. J Neural Transm. Suppl. 16, 163-172.

Houtsmuller, E. J., et al. (2002). Effects of selegiline (l-deprenyl) during smoking and short-term abstinence. Psychopharmacology, 163: 213-220.

Houtsmuller, E. J., et al. (2004). Transdermal selegiline and intravenous cocaine: safety and interactions. Psychopharmacology, 172: 31-40.

Tariot, P.N., et al., (1987), L-deprenyl in Alzheimer's disease, Preliminary evidence . . . , Arch General Psychiatry, vol. 44, pp. 427-433.

Koob, G. F., (2003), "Alcoholism: Allostasis and Beyond," Alcoholism: Clinical and Experimental Research, 27, pp. 232-243.

Physicians' Desk Reference, 51 Edition, 1997, p. 2802-2803.

Baker, J., et al., 2007 Disulfiram effects on responses to intravenous cocaine administration, Drug and Alcohol Dependence 87, 202-209.

Bartzokis, George, et al., 1999 Selegiline Effects on Cocaine-Induced Changes in Medial . . . , Neuropsychopharmacology 20, No. 6 published by Elsevier Science.

Singh, R., et al., 1995 Acute Organic Brain Syndrome after Fluoxetine Treatment Am. J. Psychiatry 152: 2 p. 295.

Carroll, K., et al., 1998 Treatment of Cocaine and Alcohol Dependence with Psychotherapy and Disulfiram in Addiction 93(5), 713-728.

Carroll, K. et al., 2004 Efficacy of Disulfiram and Cognitive Behavior Therapy in Cocaine-Dependent Outpatients, in Arch Gen Psychiatry 61, 264-272,.

Ekstedt, B., et al., 1979 Does the B Form Selective Monoamine Oxidase Inhibitor Lose Selectivity by Long Term Treatment? in Biochemical Pharmacology 28, 919-923.

Elkashef, A., et al., 2006 Double-blind, Placebo-controlled Trial of Selegiline Transdermal System (STS) . . . In Drug and Alcohol Dependence 85 191-197.

Felner, A., et al., 1979 Cumulative Effects of Irreversible MAO Inhibitors in Vivo in Biochemical Pharmacology 28 995-1002.

George, T., et al., 2000 Disulfiram versus Placebo for Cocaine Dependence in Buprenorphine-Maintained Subjects: A Preliminary Trial in Biol Psychiatry 47 1080-1086.

Hameedi, F., et al., 1995 Behavioral, Physiological, and Pharmacological Interaction of Cocaine and Disulfiram in Humans in Biol Psychiatry 37 560-563.

Harris, D., et al., 2009 A Phase I Trial of Pharmacologic Interactions . . . in BMC Clinical Pharm 9: 13. (available at http://www.biomedcentral.com/1472-690 Apr. 9, 2013).

Karamanakos, P., et al., 2001 Differentiation of Disulfiram Effects on Central Catecholamines and Hepatic Ethanol Metabolism in Pharmacology & Toxicology 88, 106-110.

McCance-Katz, E., et al., 1998 Chronic Disulfiram Treatment Effects on Intranasal Cocaine Administration: Initial Results in Biol. Psychiatry 43, 540-543.

Newton, T., et al., 1999 Effects of Selegiline Pretreatment on Response to Experimental Cocaine Administration in Psychiatry Research 87, 101-106.

Petrakis, I., et al., 2000 Disulfiram Treatment for Cocaine Dependence in Methadone-maintained Opioid Addicts in Addiction 95, 219-228.

Schiffer, W., et al., 2003 Selegiline Potentiates Cocaine-Induced Increases in Rodent Nucleus Accumbens Dopamine in Synapse 48, 35-38.

Sofuoglu, M., et al., 2008 Disulfiram Enhances Subjective Effects of Dextroamphetamine in Humans in Pharmacology, Biochemistry and Behavior 90, 394-8.

Yang, H. et al., 1973 beta.-Phenylethylamine: A Specific Substrate for Type B Monoamine Oxidase of Brain in J. Pharm. Exp. Therapeutics 187, 365-371.

Yasar, S., et al., 2005 Discriminative Stimulus and Reinforcing Effects of p-fluoro-L-deprenyl in Monkeys in Psychopharmacology 182, 95-103.

* cited by examiner

COMPOSITIONS AND METHODS FOR INCREASING COMPLIANCE WITH THERAPIES USING ALDEHYDE DEHYDROGENASE INHIBITORS AND TREATING ALCOHOLISM

CROSS-REFERENCE TO RELATED APPLICATIONS

This patent application is a divisional of U.S. patent application Ser. No. 12/145,792, filed on Jun. 25, 2008 (U.S. Pat. No. 8,093,300), which is a divisional of U.S. patent application Ser. No. 10/287,153, filed on Nov. 4, 2002. Provisional Application is U.S. Patent Application Ser. No. 60/338,901, filed Nov. 5, 2001. The entire content of the related applications is incorporated herein.

BACKGROUND OF THE INVENTION

1. Field of the Invention

The present invention relates to compositions and methods for increasing patient compliance with therapies comprising the administration of aldehyde dehydrogenase inhibitors, and for preventing, ameliorating or treating alcoholism. Such compositions and methods may be used to facilitate alcohol cessation, and may comprise a combination of aldehyde dehydrogenase inhibitors and monoamine oxidase inhibitors.

2. Description of the Related Art

Alcohol is a commonly abused drug. According to the Diagnostic and Statistical Manual of Mental Disorders (DSM-IV), problematic alcohol use is divided into alcohol abuse and alcohol dependence.

Alcohol abuse involves recurrent alcohol consumption that negatively affects one's life, whereas alcohol dependence includes alcohol abuse and additionally symptoms of tolerance and withdrawal [McRae et al., "Alcohol and Substance Abuse," In: Advances in the Pathophysiology and Treatment of Psychiatric Disorders: Implications for Internal Medicine, 85(3):779-801 (2001); Swift, R. M., New England J. Med 340:1482-1490 (1999); Kick, S., Hospital Practice 95-106 (1999)]. In 1997, the estimated lifetime prevalence for alcohol abuse was 9.4% and for alcohol dependence was 14.1%, with men having significantly higher rates of dependence than women [McRae et al., supra]. Alcohol abuse and dependence commonly lead to other problems such as alcohol-related violence, motor vehicle accidents, and medical consequences of chronic alcohol ingestion including death [McRae et al., supra; Swift, supra].

One of the pharmacotherapies that have been suggested for treating alcoholism, including facilitating alcohol cessation, is the administration of agents that inhibiting the enzyme aldehyde dehydrogenase (ALDH), an enzyme involved in the removal of acetaldehyde, a toxic metabolite of alcohol. Examples of ALDH inhibitors include, e.g., disulfiram, coprine, cyanamide, 1-aminocyclopropanol (ACP), daidzin, cephalosporins, antidiabetic sulfonyl ureas, metronidazole, and any of their metabolites or analogs exhibiting ALDH-inhibiting activity including, e.g., S-methyl N,N-diethyldithiocarbamate, S-methyl N,N-diethyldithiocarbamate sulfoxide, and S-methyl N,N-diethylthiocarbamate sulfoxide. Patients who consume such inhibitors of ALDH experience mild to severe discomfort if they ingest alcohol. The efficacy of therapies using ALDH inhibitors depends on the patient's own motivation to self-administer the ALDH inhibitors, e.g., oral forms of the inhibitors, or to receive additional therapies, e.g., DEPO forms of disulfiram. In fact, patient compliance is a significant problem with these types of therapies.

Although multiple forms of ALDH exist, ALDH-I (also known as ALDH-2) and ALDH-II (also known as ALDH-1) are the major enzymes responsible for the oxidation of acetaldehyde. ALDH-I has a higher affinity for acetaldehyde than ALDH-II, and is thought to be the primary enzyme involved in alcohol detoxification [Keung, W. M., et al., Proc. Natl. Acad. Sci. USA 95:2198-2203 (1998)]. The discovery that 50% of the Asian population carries a mutation in ALDH-I that inactivates the enzyme, together with the low occurrence of alcohol abuse in this population supports the contention that it is this isozyme of ALDH that is primarily responsible for alcohol detoxification. Recent studies also implicate ALDH-I in the metabolism of monoamine neurotransmitters such as serotonin (5-HT) and dopamine (DA) [Keung, W. M., et al., Proc. Natl. Acad. Sci. USA 95:2198-2203 (1998)].

Disulfiram, also known as tetraethylthioperoxydicarbonic diamide, bis-diethylthiocarbamoyl disulfide, tetraethylthiuram disulfide, Cronetal™, Abstenil™, Stopetyl™, Contrain™, Antadix™, Anietanol™, Exhoran™, ethyl thiurad, Antabuse™, Etabuse™, RO-sulfiram, Abstinyl™, Thiuranide™, Esperal™, Tetradine™, Noxal™, Tetraeti™. [Swift, supra], is a potent irreversible inhibitor of ALDH-II and inhibits ALDH-I only slightly. Recent studies suggest that the inhibition of ALDH-I by disulfiram occurs indirectly via its metabolites, e.g., S-methyl-N,N-diethylthiocarbamate sulfoxide (DETC-MeSO) [Yourick et al., Alcohol 4:463 (1987); Yourick et al., Biochem. Pharmacol. 38:413 (1989); Hart et al., Alcohol 7:165 (1990); Madan et al., Drug Metab. Dispos. 23:1153-1162 (1995)]. Ingestion of alcohol while taking disulfiram results in the accumulation of aldehydes, which causes tachycardia, flushing, diaphoresis, dyspnea, nausea and vomiting (also known collectively as the disulfiram or disulfiram-ethanol reaction).

Although disulfiram has been available in the United States for many decades, patients frequently have difficulty complying with disulfiram treatment therapies. One reason for poor compliance is the lack of motivation for the patient to continue to take disulfiram, that is, other than self-motivation (i.e., there is no positive reinforcement for taking disulfiram). Another reason is because of the discomfort that arises if the patient ingests alcohol during disulfiram therapy [McRae et al., supra; Swift, R. M., supra; Kick, S., supra]. In fact, disulfiram has not proven to be useful in maintaining long-term sobriety [Kick, supra].

Coprine (N5-(hydroxycyclopropyl)-L-glutamine) has been shown to inhibit ALDH via its active metabolite, 1-aminocyclopropanol (ACP). U.S. Pat. No. 4,076,840 describes the synthesis and use of cyclopropyl benzamides, including coprine, for the treatment of alcoholism. In rat studies, coprine effectively suppressed ethanol consumption, and was shown to be a more potent inhibitor of ALDH as compared to disulfiram [Sinclair et al., Adv. Exp. Med. Biol. 132:481-487 (1980); U.S. Pat. No. 4,076,840].

Cyanamide has been described as an alcohol-sensitizing agent that is less toxic than disulfiram [Ferguson, Canad. M.A.J. 74:793-795 (1956); Reilly, Lancet 911-912 (1976)]. Although cyanamide is unable to inhibit either ALDH-I or ALDH-II in vitro, a reactive product of cyanamide catabolism inhibits both isozymes in vivo, indicating that cyanamide inhibits ALDH via a reactive species [DeMaster et al., Biochem. Biophys. Res. Com. 107:1333-1339 (1982)]. Cyanamide has been used for treating alcoholism but has not been approved in the U.S. Citrated calcium cyanamide is marketed in other countries as Temposil™, Dipsane™ and Abstem™, and plain cyanamide is marketed as Colme™ in Spain [See, U.S. Pat. No. 6,255,497].

Daidzin is a selective potent reversible inhibitor of ALDH-I, originally purified from an ancient Chinese herbal treatment for alcohol abuse. Its analogs include daidzein-7-O-[.omega.-carboxynonyl] ether (deczein), daidzein-7-O-[.omega.-carboxyhexyl] ether (hepzein), daidzein-7-O-[.omega.-carboxypentyl] ether (hexzein), daidzein, puerarin, and dicarboxymethyl-daidzein [Keung, Chemico-Bio. Int. 130-132:919-930 (2001)]. U.S. Pat. Nos. 5,204,369; 5,886,028; 6,121,010; and 6,255,497 describe methods for treating alcohol dependence or abuse using these compounds.

One of the major problems associated with therapies using ALDH inhibitors is ensuring patient compliance with the regimen. According to applicant's knowledge, there have been no teachings that suggest pharmacotherapies that adequately address this problem. For example, WO 99/21540 describes the administration of disulfiram in combination with compounds that bind to the D1 and/or D5 receptors and mimic dopamine to reduce craving for addictive substances in mammals. However, WO 99/21540 does not suggest pharmacotherapy for ensuring patient compliance with the regimen, which is important for the success of the treatment.

Another pharmacotherapy that has been suggested for treating alcoholism involves the inhibition of monoamine oxidases (MAOs). MAOs catalyze the oxidation of a variety of monoamines, including epinephrine, norepinephrine, serotonin and dopamine. MAOs are iron containing enzymes that exist as two isozymes A (MAOA) and B (MAOB). Various publications have described treatments for alcoholism using MAOB inhibitors [e.g, WO 92/21333, WO 96/37199]. WO 96/35425 discusses a treatment for alcoholism using a selective MAOB inhibitor in combination with a partial agonist of the 5-TH1A receptor. WO 00/71109 discusses a treatment for alcohol withdrawal symptoms using the MAOB inhibitor desmethylselegiline in combination with a second drug that treats alcohol withdrawal symptoms. U.S. Pat. No. 6,239,181 describes methods for alleviating symptoms associated with alcoholic neuropathy by administering the MAOB inhibitor, selegiline. However, none of the above references teach or suggest the use of MAOB inhibitors in therapies using ALDH inhibitors. Moreover, none of these references teach that MAOB inhibitors have a sustained effect on ensuring patient compliance with other therapies.

The present invention provides a solution for the deficiencies in traditional therapies using ALDH inhibitors to stop, prevent or reduce recidivism, thus, promoting compliance. The present invention also provides unexpectedly new and better compositions and methods for treating diseases that require the self-administration of an ALDH inhibitor.

SUMMARY OF THE INVENTION

The present invention provides compositions and methods for preventing, treating or reducing alcoholism comprising administering a therapeutically effective amount of an ALDH inhibitor in combination with an MAOB inhibitor.

There is provided in one embodiment of the present invention compositions and methods for increasing the rate of continuous abstinence, delaying resumption of abuse or dependence and/or preventing relapses in patients being treated for alcoholism.

There is further provided a method for increasing patient compliance with therapies that require self-administration of an ALDH inhibitor comprising the step of administering a therapeutically effective amount of a MAOB inhibitor.

According to one embodiment of the invention, the patient to be treated suffers from a disease requiring treatment with an ALDH inhibitor and consumes or can consume alcohol during therapy. The therapy does not involve forcing the patient to intake alcohol as part of the treatment. According to one preferred embodiment of this invention, the patient to be treated is suffering from alcoholism.

A composition according to the latter embodiment of the invention comprises an MAOB inhibitor and an ALDH inhibitor. The ALDH inhibitor may inhibit ALDH-I. The ALDH inhibitor may be, e.g., disulfiram, coprine, cyanamide, 1-aminocyclopropanol (ACP), daidzin, cephalosporins, antidiabetic sulfonyl ureas, metronidazole, or any of their metabolites or analogs exhibiting ALDH-inhibiting activity including, e.g., S-methyl N,N-diethyldithiocarbamate, S-methyl N,N-diethyldithiocarbamate sulfoxide, or S-methyl N,N-diethylthiocarbamate sulfoxide. In a more preferred embodiment, the ALDH inhibitor is disulfiram or an ALDH-inhibiting metabolite thereof. According to one preferred embodiment, the amount of disulfiram or an ALDH-inhibiting metabolite thereof administered is 500 mg per day.

In one embodiment, the MAOB inhibitor is, e.g., selegiline, pargyline, desmethylselegiline, rasagiline [R(+) N-propargyl-laminoindan]- , 3-N-phenylacetylamino-2,5-piperidinedione or caroxyazone. In a more preferred embodiment, the MAOB inhibitor is selegiline. According to one preferred embodiment, the amount of selegiline administered is 15 mg or less per day.

DETAILED DESCRIPTION OF THE INVENTION

An MAOB inhibitor according to this invention is a compound that inhibits MAOB but causes much less or no inhibition of MAOA activity, or a compound that selectively inhibits MAOB (e.g., within a particular dosage range). Hereinafter, the activity of an MAOB inhibitor as used according to this invention will be referred to as "selective MAOB inhibitor activity."

In one embodiment, the MAOB inhibitor is selected from the group consisting of selegiline (Jumex®, Jumexal® Carbex®, Eldepryl®, Movergan®; Aptapryl®, Anipryl®; Eldeprine®; Plurimen®), desmethylselegiline, pargyline (Eudatin®, Supirdyl®, Eutonyl®) [U.S. Pat. No. 3,155,584], rasagiline [R(+)N-propargyl-laminoindan], 3-N-phenylacetylamino-2,5-piper-idinedione, caroxyazone, AGN-1135 [WO 92/21333], MDL 72195 [WO 92/21333], J 508 [WO 92/21333], lazabemide [WO 00/45846], milacemide [WO 00/45846], IFO [WO 00/45846], mofegiline [WO 00/45846], and 5-(4-(4,4,4-trifluorobut-oxy)phenyl)-3-(2-methoxyethyl)-1,3,4-oxadiazol-2(3H)-one [WO 00/45846]. In another embodiment, prodrugs or metabolites of the MAOB inhibitors are contemplated. Said metabolite should have substantially the same or better selective MAOB inhibitor activity as its unmetabolized form.

A prodrug of a MAOB inhibitor is a derivatized MAOB inhibitor that is metabolized in vivo into the active inhibitory agent. Prodrugs according to this invention preferably have substantially the same or better therapeutic value than the underivatized MAOB inhibitor. For example, a prodrug useful according to this invention can improve the penetration of the drug across biological membranes leading to improved drug absorption; prolong duration of the action of the drug, e.g., slow release of the parent drug from the prodrug and/or decrease first-pass metabolism of the drug; target the drug action; improve aqueous solubility and stability of the drug (e.g., intravenous preparations, eyebrows etc.); improve topical drug delivery (e.g., dermal and ocular drug delivery);

improve the chemical and/or enzymatic stability of drugs (e.g., peptides); or decrease side effects due to the drug. Methods for making prodrugs are readily known in the art.

The term "MAOB inhibitor" according to this invention or metabolite thereof, as used herein includes pharmaceutically acceptable salts of those compounds. Pharmaceutically acceptable salts of MAOB inhibitors useful according to the methods of this invention are salts prepared from pharmaceutically acceptable reagents. In one embodiment, said pharmaceutically acceptable salt is a hydrochloride salt.

Methods known in the art for evaluating the activity of MAOB and MAOA can be used for selecting MAOB inhibitors according to this invention. For example, blood samples can be drawn to determine platelet MAO activity using radio-labelled benzylamine or phenylethylamine. (i.e., evaluating MAOB inhibitory activity). [Murphy, D. L., et al., Psychopharm. 62:129-132 (1979); Murphy, D. L., et al., Biochem. Med. 16:254-265 (1976); all incorporated by reference herein] In one embodiment, MAOB activity is decreased greater than 80% compared to MAOB enzyme activity before treatment. In a preferred embodiment, MAOB activity is decreased greater than 90% or 95% compared to MAOB activity before treatment.

MAOA inhibitory activity can, for example, be evaluated by measuring levels of 3-methoxy-4-hydroxyphenylglycol (MHPG) or 5-hydroxyindoleacetic acid (5-HIAA) in the plasma of blood or in cerebral spinal fluid (CSF) by using gas chromatography-mass spectroscopy (gc-ms). [Murphy, D. L., et al., Clinical Pharmacology in Psychiatry, 3rd Series., Eds. Dahl, Gram, Paul, and Potter, Springer-Verlag: 1987; Major, L. F., et al., J. Neurochem. 39:229-231 (1979); Jimerson, D. C., et al., Biomed. Mass. Spectrom. 8:256-259 (1981); all incorporated by reference herein]. In one embodiment, after administration of the MAOB inhibitor, plasma MHPG levels should not be reduced lower than 45% of pretreatment levels of plasma MHPG. In a preferred embodiment, after administration of the MAOB inhibitor, plasma MHPG or CSF 5-HIAA levels should not be reduced more than 80% of pretreatment levels of MHPG or 5-HIAA levels, respectively.

ALDH inhibitors according to the invention are compounds that are capable of inhibiting the activity of one or more of the several isozymes of ALDH, e.g., ALDH-I and ALDH-II. According to one embodiment, the ALDH is involved in alcohol metabolism. ALDH inhibitors according to this invention include, e.g., disulfiram, coprine, cyanamide, 1-aminocyclopropanol (ACP), daidzin, cephalosporins, antidiabetic sulfonyl ureas, metronidazole, and any of their metabolites or analogs exhibiting ALDH-inhibiting activity. In another embodiment, the ALDH inhibitor is disulfiram or an ALDH-inhibiting metabolite thereof. Such metabolites include, e.g., S-methyl N,N-diethyldithiocarbamate, S-methyl N,N-diethyldithiocarbamate sulfoxide, and S-methyl N,N-diethylthiocarbamate sulfoxide.

The term "ALDH inhibitor" according to the invention or metabolite thereof, as used herein, includes pharmaceutically acceptable salts of those compounds.

The term "alcoholism" according to the invention includes alcohol abuse and alcohol dependence as described below.

The term "alcohol abuse" is defined in the Diagnostic and Statistical Manual of Mental Disorders (DSM-IV). Alcohol abuse as a maladaptive pattern of alcohol use that leads to clinically significant impairment or distress. Symptoms include one or more of the following occurring within a 12-month period: (1) recurrent alcohol use that results in a failure to fulfill major role obligations at work, school or home; (2) recurrent alcohol use in physically hazardous situations; (3) recurrent alcohol-related legal problems; and (4) continued alcohol use despite having persistent or recurrent social or interpersonal problems caused or exacerbated by the effects of the substance [McRae et al., supra; Swift, R. M., supra; Kick, S., supra].

Alcohol dependence occurs when symptoms of abuse are accompanied by three or more of the following: (1) tolerance defined by either: (a) a need for markedly increased amounts of alcohol to achieve intoxication or desired effect, or (b) markedly diminished effect with continued use of the same amount of alcohol; (2) withdrawal manifested by either: (a) characteristic withdrawal syndrome for alcohol or (b) alcohol taken to relieve or avoid withdrawal symptoms; (3) alcohol taken in larger amounts over a longer period than as intended; (4) a persistent desire or unsuccessful efforts to reduce or control drinking; (5) much time spent in activities necessary to obtain alcohol, use alcohol, or recover from its effects; (6) important social, occupational, or recreational activities being given up or reduced because of drinking; and (7) continued use despite knowledge of having a persistent or recurrent physical or psychological problem caused or exacerbated by alcohol [McRae et al., supra; Swift, R. M., supra; Kick, S., supra].

Alcohol abuse or dependence can also result in other symptoms including dyspepsia or epigastric pain, headache, diarrhea, difficulty in sleeping, fatigue, unexplained weight loss, apparent malnutrition, easy bruising, increased mean corpuscular volume, elevated transaminase levels (especially an aspartate transaminase level greater than of alanine transaminase), elevated y-glutamyl transferase levels, iron-deficiency anemia, hepatomegaly, jaundice, spider angiomata, ascites, and peripheral edema. Behavioral symptoms associated with alcohol abuse or dependence include absenteeism from work or school, increasing irritability, difficulties with relationships, verbal or physical abuse, and depression [McRae et al., supra; Swift, R. M., supra; Kick, S., supra].

Alcoholism is often diagnosed using questionnaires, known to those of ordinary skill in the art, which are structured to obtain information related to the symptoms of alcohol abuse and/or dependence as outlined by the Diagnostic and Statistical Manual of Mental Disorders (DSM-IV). The most commonly used screening test used for detecting alcohol abuse or dependence is the CAGE questionnaire [Kick, S., supra]. Alcoholics Anonymous describes another questionnaire.

A patient to be treated for, or protected against, the onset of alcoholism according to this invention can be a human, including children and adults, who are susceptible to or are suffering from alcoholism or who are being treated for alcoholism and are susceptible to experiencing relapses. A patient who is having difficulty complying with, or is being induced to comply with, treatments using ALDH inhibitors or their active metabolites according to this invention can be a human, including children and adults.

Compositions according the present invention comprise a pharmaceutically acceptable carrier together with an ALDH inhibitor and an MAOB inhibitor. According to one embodiment, the ALDH inhibitor is disulfiram, or a metabolite or prodrug thereof. According to another embodiment, the composition comprises 500 mg, 250 mg, 125 mg, or 60 mg of disulfiram, or metabolite or prodrug thereof. According to yet another embodiment, the MAOB inhibitor is selegiline, or a metabolite or prodrug thereof. According to a further embodiment, the composition comprises 15 mg or less of selegiline, or metabolite or prodrug thereof.

In a preferred embodiment, the composition comprises 500 mg, 250 mg, 125 mg or 60 mg of disulfiram, or metabolite or prodrug thereof, and 15 mg or less of selegiline, or metabolite or prodrug thereof. In a more preferred embodiment, the composition comprises about 60 mg of disulfiram, or a metabolite or prodrug thereof, and about 2 mg of selegiline, or a metabolite or prodrug thereof.

The effective dosage of a composition of the invention administered to a patient is at least an amount required to minimize, reduce or eliminate one or more symptoms associated with preventing or treating alcoholism, typically one of the symptoms discussed above. The magnitude of a prophylactic or therapeutic dose of the composition of the invention in the treatment of a patient will vary with the symptoms being exhibited, the severity of the patient's affliction, the desired degree of therapeutic response, the route of administration, and the concomitant therapies being administered. The dose and dose frequency will also vary according to the age, weight and response of the individual patient. Generally, however, treatment for alcoholism will be ongoing, although the intensity of treatment can vary depending on the patient's condition and exposure to biochemical and environmental stimuli that can warrant a variation on the treatment. Dosages can be administered in a single or multiple dosage regimen.

According to one preferred embodiment of the invention, the composition comprising 500 mg, 250 mg, 125 mg or 60 mg of disulfiram and 15 mg or less selegiline is administered twice a day, in the morning and at noon or late afternoon. In another preferred embodiment, a composition comprising about 125 mg of disulfiram and about 5 mg of selegiline is administered twice a day, in the morning and at noon or late afternoon.

Selegiline can be administered twice a day, in the morning and at noon or late afternoon. An initial daily non-oral dose can be at least about 0.01 mg per kg of body weight, calculated on the basis of the free secondary amine, with progressively higher doses being employed depending upon the response to therapy. The final daily dose can be between about 0.05 mg/kg of body weight to about 0.15 mg/kg of body weight (all such doses being calculated in the basis of the free secondary amine).

The present invention when employing selegiline is not limited to a particular form of selegiline and the drug can be used either as a free base or as a pharmaceutically acceptable acid addition salt. In the latter case, the hydrochloride salt is preferred. However, other salts useful in the invention include those derived from organic and inorganic acids such as, without limitation, hydrobromic acid, phosphoric acid, sulfuric acid, methane sulfonic acid, acetic acid, tartaric acid, lactic acid, succinic acid, citric acid, malic acid, maleic acid, aconitic acid, salicylic acid, thalic acid, embonic acid, enanthic acid, and the like.

The treating physician will know how to increase, decrease or interrupt treatment based upon the patient's response. Improvement for alcoholics or potentially relapsing alcoholics can be assessed by observing increased abstinence from consuming alcohol by the patient, following the methods of this invention, as compared to patients where therapy did not comprise the co-administration of a MAOB inhibitor. Improvement in compliance with self-administering ALDH inhibitors can be assessed by observing the increased duration over which patients, following the methods of this invention, take the ALDH inhibitor as compared to patients whose therapy did not comprise the co-administration of an MAOB inhibitor.

Any suitable route of administration can be employed for providing the patient with an effective dosage of a composition of this invention. For example, oral, peroral, buccal, nasal, pulmonary, vaginal, lingual, sublingual, rectal, parenteral, transdermal, intraocular, intravenous, intraarterial, intracardial intramuscular, intraperitoneal, intracutaneous, subcutaneous, sublingual, intranasal, intramuscular, and intrathecal administration and the like can be employed as appropriate. The term parenteral as used herein includes subcutaneous, intracutaneous, intravenous, intramuscular, intraarticular, intrasynovial, intrasternal, intrathecal, intralesional and intracranial injection or infusion techniques. According to one preferred aspect of this invention, the route of administration is the oral route.

The composition can be conveniently presented in unit dosage form and prepared by any of the methods well-known in the art of pharmacy. Dosage forms can include tablets, scored tablets, coated tablets, pills, caplets, capsules (e.g., hard gelatin capsules), troches, dragees, powders, aerosols, suppositories, parenterals, dispersions, suspensions, solutions, transdermal patches and the like, including sustained release formulations well known in the art. In one preferred embodiment, the dosage form is a scored tablet or a transdermal patch. U.S. Pat. No. 5,192,550, incorporated herein by reference, describes a dosage form for selegiline comprising an outer wall with one or more pores, in which the wall is impermeable to selegiline but permeable to external fluids. This dosage form can have applicability for oral, sublingual or buccal administration.

The compositions of this invention can be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient (i.e., ALDH inhibitor and/or MAOB inhibitor) is combined with emulsifying and suspending agents. If desired, certain sweetening and/or flavoring and/or coloring agents can be added.

The compositions according to this invention can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant such as Ph. Helv or a similar alcohol.

Methods for making transdermal patches including selegiline transdermal patches have been described in the art. [See e.g., U.S. Pat. Nos. 4,861,800; 4,868,218; 5,128,145; 5,190,763; and 5,242,950; and EP-A 404807, EP-A 509761, EP-A 593807, and EP-A 5509761, all of which are incorporated by reference herein.]

Compositions of this invention can also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

Patients can be regularly evaluated by physicians, e.g., once a week, to determine whether there has been an improvement in symptoms and whether the dosage of the composition of the invention needs to be adjusted.

According to the methods of this invention, the MAOB inhibitor can be included in the composition comprising the ALDH inhibitor. Alternatively, the MAOB inhibitor can be administered simultaneously with the composition comprising the ALDH inhibitor, or at any time during the treatment of the patient with the ALDH inhibitor.

The various terms described above such as "therapeutically effective amount," are encompassed by the above-described dosage amounts and dose frequency schedule. Generally, a therapeutically effective amount of an MAOB inhibitor is that amount at which MAOB is inhibited but MAOA exhibits slight or no reduction in activity in the patient. Slight reduction in activity preferably comprises less than about 30% reduction in activity, more preferably less than about 20% reduction in activity, and yet more preferably less than about 10% reduction in activity. In one embodiment, the dosage of selegiline is an amount equal to or less than 15 mg per day. In another embodiment, the dosage of pargyline is equal to or less than 30 mg/day.

Throughout this specification, the word "comprise" or variations such as "comprises" or "comprising" will be understood to imply the inclusion of a stated integer or group of integers but not the exclusion of any other integer or group of integers.

Statement Regarding Preferred Embodiments

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

What is claimed is:

1. An oral composition for treating or reducing alcoholism in a patient comprising a monoamine oxidase B (MAOB) inhibitor selected from selegiline and an aldehyde dehydrogenase (ALDH) inhibitor selected from disulfiram wherein the amount of selegiline is 5 mg to 10 mg per day, and the amount of disulfiram is about 250 mg per day.

2. The composition according to claim 1, wherein the composition is formulated as a capsule, or a tablet.

3. The composition according to claim 1, wherein the composition comprises a therapeutically effective single dosage.

4. The composition according to claim 1, wherein the patient is human.

5. An oral composition for enhancing patient compliance with regimen for treatment of alcoholism, the composition comprising a monoamine oxidase B (MAOB) inhibitor selected from selegiline and an aldehyde dehydrogenase (ALDH) inhibitor selected from disulfiram, wherein the amount of selegiline is 5 mg to 10 mg per day, and the amount of disulfiram is about 250 mg per day.

6. The composition according to claim 5, wherein the composition is administered as a capsule, or a tablet.

7. The composition according to claim 5, wherein the patient is human.

8. The composition according to claim 5, wherein the composition comprises a therapeutically effective single dosage.

9. The composition according to claim 1 or 5, wherein the monoamine oxidase B (MAOB) inhibitor is in pharmaceutically acceptable salt form.

10. The composition according to claim 1 or 5, wherein the aldehyde dehydrogenase (ALDH) inhibitor is in pharmaceutically acceptable salt form.

11. A self-administration composition for treatment of alcoholism comprising a single dose formulated in a one a day capsule or tablet containing a therapeutically effective amount of 5 mg to 10 mg selegiline and about 250 mg disulfiram.

* * * * *